US009316659B2

(12) United States Patent
Dumitrescu

(10) Patent No.: US 9,316,659 B2
(45) Date of Patent: Apr. 19, 2016

(54) METHOD AND SYSTEM FOR TRANSPORTING SAMPLE TUBES

(71) Applicant: Siemens Healthcare Diagnostics Inc., Tarrytown, NY (US)

(72) Inventor: Nicolae Dumitrescu, Stamford, CT (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/400,270

(22) PCT Filed: May 7, 2013

(86) PCT No.: PCT/US2013/039949
§ 371 (c)(1),
(2) Date: Nov. 10, 2014

(87) PCT Pub. No.: WO2013/169778
PCT Pub. Date: Nov. 14, 2013

(65) Prior Publication Data
US 2015/0122614 A1 May 7, 2015

Related U.S. Application Data

(60) Provisional application No. 61/645,768, filed on May 11, 2012.

(51) Int. Cl.
*B65G 17/46* (2006.01)
*G01N 35/04* (2006.01)
*B65G 54/02* (2006.01)

(52) U.S. Cl.
CPC .............. *G01N 35/04* (2013.01); *B65G 17/46* (2013.01); *B65G 54/02* (2013.01); *B65G 54/025* (2013.01); *G01N 2035/047* (2013.01); *G01N 2035/0477* (2013.01); *G01N 2035/0484* (2013.01)

(58) Field of Classification Search
CPC ...... B65G 17/46; B65G 54/025; B65G 54/02; G01N 35/04

USPC .................. 198/690.1, 465.1, 465.2
See application file for complete search history.

(56) References Cited

U.S. PATENT DOCUMENTS 2,940,581 A     6/1960   Chebuhar
4,235,187 A *  11/1980   Mirza ................. B05C 7/00
                                                    198/690.1

(Continued)

FOREIGN PATENT DOCUMENTS

JP      2007 039237 A    2/2007
WO        03/052048 A2   5/2003

OTHER PUBLICATIONS

PCT International Search Report and Written Opinion dated Aug. 30, 2013 (8 Pages).

(Continued)

*Primary Examiner* — James R Bidwell
(74) *Attorney, Agent, or Firm* — Pepper Hamilton LLP

(57) ABSTRACT

A sample tube transport system that includes a track adapted to provide a path for one or more carriers between a plurality of modules. The system includes at least one upper conveyor system having an upper belt configured to wrap around a first upper pulley and a second upper pulley, and a plurality of upper magnets affixed to the upper belt to move the one or more carriers along the track adjacent the upper belt. The at least one lower conveyor system includes a lower belt spaced vertically below the upper belt and configured to wrap around the first lower pulley and the second lower pulley, and a plurality of lower magnets affixed to the lower belt. Each of the plurality of lower magnets are positioned to attract and move the one or more carriers along the track adjacent the lower belt.

20 Claims, 8 Drawing Sheets

(56) References Cited

U.S. PATENT DOCUMENTS

| | | | | |
|---|---|---|---|---|
| 5,224,585 A | * | 7/1993 | Blanco | B01L 9/06 198/690.1 |
| 5,423,410 A | * | 6/1995 | Keller | B65G 47/252 198/690.1 |
| 5,720,377 A | | 2/1998 | Lapeus et al. | |
| 6,241,077 B1 | * | 6/2001 | Bertrams | B65G 21/2018 198/690.1 |
| 7,946,414 B2 | | 5/2011 | Greene | |
| 2009/0071803 A1 | * | 3/2009 | Zhang | B65G 17/46 198/853 |
| 2009/0242356 A1 | | 10/2009 | Layne | |

OTHER PUBLICATIONS

Extended EP Search Report dated Dec. 8, 2015 of corresponding European Application No. 13787671.0, 4 Pages.

* cited by examiner

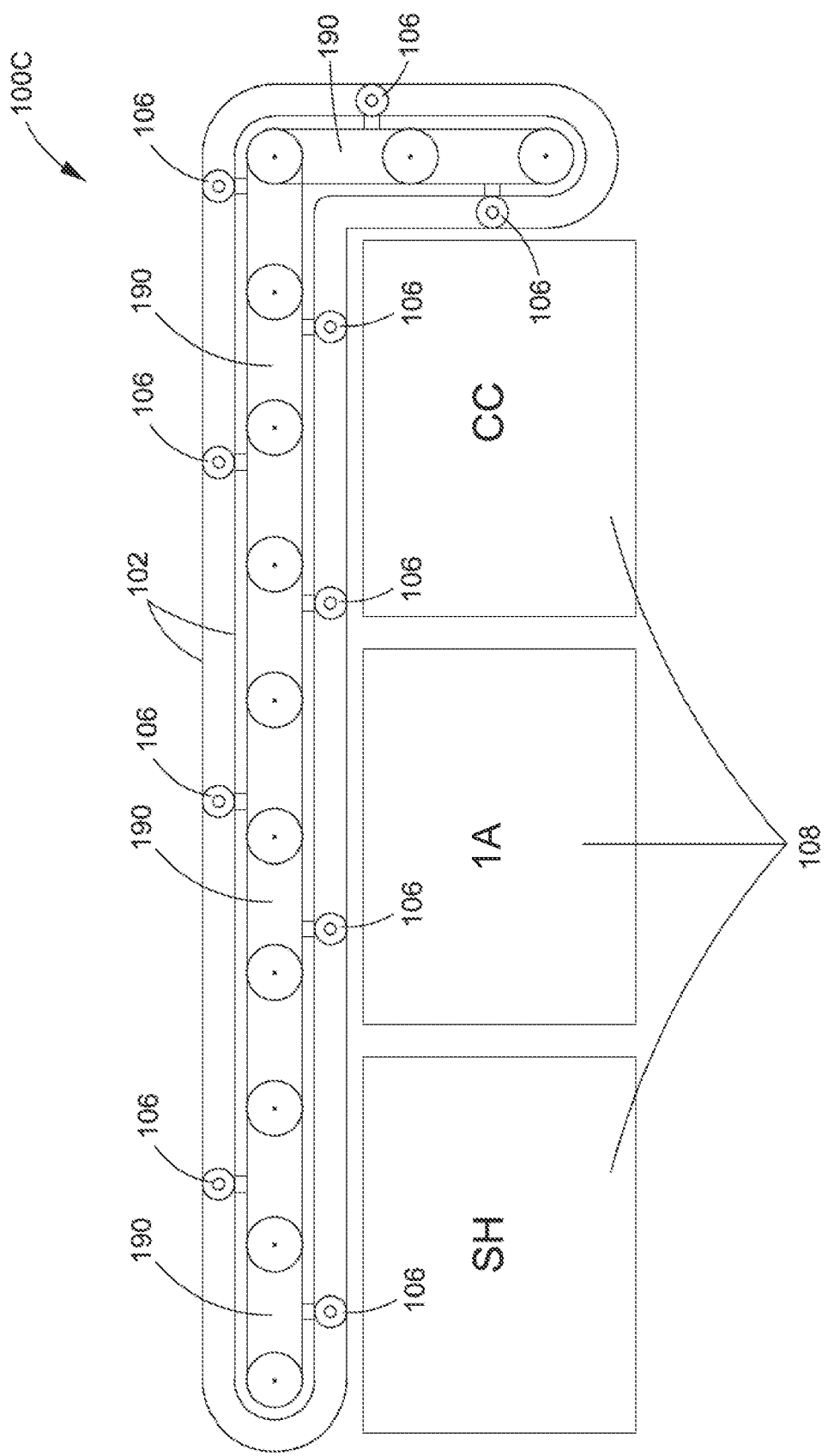

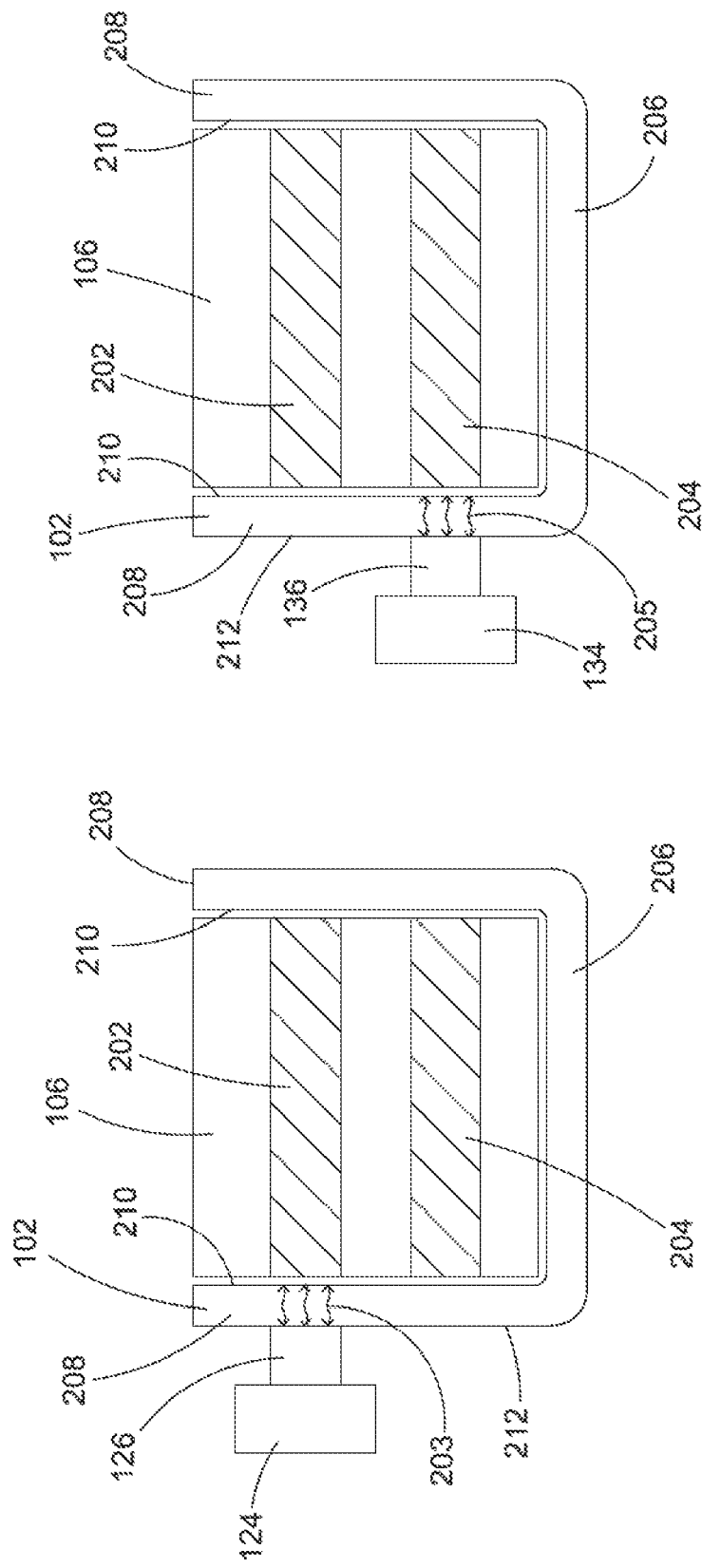

METHOD AND SYSTEM FOR TRANSPORTING SAMPLE TUBES

CROSS-REFERENCE TO RELATED APPLICATIONS

This application claims priority to U.S. provisional application Ser. No. 61/645,768 filed May 11, 2012, which is incorporated herein by reference in its entirety.

TECHNOLOGY FIELD

The present invention relates in general to an automation system for use in a laboratory environment and, more particularly, to systems and methods for transporting patient samples for in vitro diagnostics in a clinical analyzer.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which tubes or vials containing patient samples have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations, pipettes and testing stations (e.g., a unit that can specialize in certain types of assays or can otherwise provide testing services to the larger analyzer), which may include immunoassay (IA) and clinical chemistry (CC) stations. Some traditional IVD automation track systems comprise systems that are designed to transport samples from one fully independent module to another standalone module. This allows different types of tests to be specialized in two different stations or allows two redundant stations to be linked to increase the volume of sample throughput available.

In some conventional systems, a friction track, much like a conveyor belt, shuttles individual carrier mechanisms (carriers), sometimes called pucks, or racks of containers between different stations. Samples may be stored in test tubes that are placed into a puck by an operator or robot arm for transport between stations in an analyzer along the track.

Conventional friction track systems, however, are not scalable. Accordingly, when additional modules are added, the conventional friction track systems must typically be replaced. Because the conventional systems are large and complex, however, the replacement costs may be very expensive and tedious. Further, conventional friction track systems move back and forth in a linear direction, without the ability to change in a non-linear direction.

SUMMARY

Embodiments of the present invention are directed to a sample tube transport system that includes a track adapted to provide a path for one or more carriers between a plurality of modules. The transport system also includes at least one upper conveyor system and at least one lower conveyor system. The upper conveyor system includes a first upper pulley configured to rotate around a first axis and a second upper pulley spaced horizontally from the first upper pulley and configured to rotate around a second axis. The upper conveyor system also includes an upper belt located adjacent the track and configured to wrap around the first upper pulley and around the second upper pulley. The upper conveyor system further includes a plurality of upper magnets affixed to the upper belt. Each of the plurality of upper magnets are positioned to attract the one or more carriers for moving the one or more carriers along the track adjacent the upper belt. The at least one lower conveyor system includes a first lower pulley spaced vertically below the first upper pulley and configured to rotate around the first axis and a second lower pulley spaced horizontally from the first lower pulley and configured to rotate around a third axis. The at least one lower conveyor system also includes a lower belt spaced vertically below the upper belt, located adjacent the track and configured to wrap around the first lower pulley and around the second lower pulley. The at least one lower conveyor system further includes a plurality of lower magnets affixed to the lower belt. Each of the plurality of lower magnets are positioned to attract the one or more carriers for moving the one or more carriers along the track adjacent the lower belt.

According to one embodiment of the invention, the plurality of upper magnets are further positioned such that an upper portion of magnetic material of the one or more carriers is attracted to a corresponding upper magnet for moving the one or more carriers along the track adjacent the upper belt. The plurality of lower magnets are further positioned such that a lower portion of magnetic material of the one or more carriers is attracted to a corresponding lower magnet for moving the one or more carriers along the adjacent the lower belt.

According to an aspect of one embodiment, the upper portion of magnetic material is vertically offset from the lower portion of magnetic material.

According to another embodiment of the invention, the first axis and the second axis are arranged to form an upper conveyor system line extending between the first axis and the second axis. The first axis and the third axis are arranged to form a lower conveyor system line extending between the first axis and the third axis. The upper conveyor system line extends from the lower conveyor system line at any angle greater than 0 degrees and less than 180 degrees.

According to yet another embodiment of the invention, the first axis and the second axis are arranged to form an upper conveyor system line extending between the first axis and the second axis. The first axis and the third axis are arranged to form a lower conveyor system line extending between the first axis and the third axis. The upper conveyor system line extends from the lower conveyor system line at any angle of about 90 degrees.

According to another embodiment of the invention, the first axis and the second axis are arranged to form an upper conveyor system line extending between the first axis and the second axis. The first axis and the third axis are arranged to form a lower conveyor system line extending between the first axis and the third axis. The upper conveyor system line and the lower conveyor system line are collinear.

According to yet another embodiment of the invention, the transport system also includes a shaft coupled to the first upper pulley and the first lower pulley and configured to rotate around the first axis. According to an aspect of an embodiment, the shaft is a drive shaft coupled to an actuation device and configured to rotate the first upper pulley around the first axis and rotate the first lower pulley around the first axis.

Embodiments of the present invention are directed to a modular sample tube transport system that includes a plurality of modules for conducting processing on one or more samples and a track configured to provide at least one path for one or more sample carriers between the plurality of modules. The transport system also includes a plurality of conveyor systems having at least one upper conveyor system and at least one lower conveyor system and one or more pulley assemblies configured to be coupled between the at least one upper conveyor system and the at least one lower conveyor system. The one or more pulley assemblies has an upper pulley and a lower pulley. The plurality of conveyor systems alternate between a respective upper conveyor system and an adjacent respective lower conveyor system. The at least one upper conveyor system includes an upper belt located adjacent the track and configured to wrap around corresponding upper pulleys of the plurality of pulley assemblies. The at least one upper conveyor system also includes a plurality of upper magnets affixed to the upper belt and positioned to attract the one or more carriers for moving the one or more carriers along the track. At least one adjacent lower conveyor system includes a lower belt located adjacent the track and configured to wrap around corresponding lower pulleys of the plurality of pulley assemblies. The at least one adjacent lower conveyor system also includes a plurality of lower magnets affixed to the lower belt and positioned to attract the one or more carriers for moving the one or more carriers along the track.

According to one embodiment of the invention, the plurality of upper magnets are further positioned such that an upper portion of magnetic material of the one or more carriers is attracted to a corresponding upper magnet for moving the one or more carriers along the track adjacent the upper belt. The plurality of lower magnets are further positioned such that a lower portion of magnetic material of the one or more carriers is attracted to a corresponding lower magnet for moving the one or more carriers along the track adjacent the lower belt.

According to another embodiment of the invention, the respective upper conveyor system is non-linear to the adjacent respective lower conveyor system. According to an aspect of an embodiment of the invention, the respective upper conveyor system is orthogonal to the adjacent respective lower conveyor system.

According to yet another embodiment of the invention, the respective upper conveyor system is collinear to the adjacent respective lower conveyor system.

According to another embodiment of the invention, the one or more pulley assemblies include a common shaft coupled between the upper pulley and the lower pulley. According to an aspect of an embodiment, the common shaft is a drive shaft coupled to an actuation device and configured to rotate the upper pulley the lower pulley.

According to yet another embodiment of the invention, the track includes a bottom portion and opposing side walls spaced from each other and extending vertically from the bottom portion. At least one of the upper magnets and lower magnets moves parallel with a portion of at least one opposing side wall for moving the one or more carriers along the track.

According to another embodiment of the invention, the transport system further includes at least one path switching gate. The plurality of modules includes a first module and a second module. The at least one path includes a first path and a second path. The second path extends between the first module and the second module. The at least one switching gate is located proximate to the intersection of the first path and the second path and is configured to cause the one or more sample carriers to move along the first path or move along the second path.

Embodiments of the present invention are directed to a method for transporting sample tubes that includes rotating an upper belt, having a plurality of upper magnets affixed thereto, around a first upper pulley and around a second upper pulley by rotating the first upper pulley around a first axis and rotating the second upper pulley around a second axis. The method also includes moving one or more carriers along a track adjacent the upper belt with the plurality of upper magnets and rotating a lower belt, having a plurality of lower magnets affixed thereto, around a first lower pulley and around a second lower pulley by rotating the first lower pulley around the first axis and rotating the second upper pulley around a third axis. The method further includes moving the one or more carriers along the track adjacent the lower belt with the plurality of lower magnets.

According to an embodiment of the invention, moving the one or more carriers along the track adjacent the upper belt with the plurality of upper magnets further includes attracting upper portions of magnetic material of corresponding carriers to respective upper magnets. Moving the one or more carriers along the track adjacent the lower belt with the plurality of lower magnets further includes attracting lower portions of magnetic material of corresponding carriers to respective lower magnets.

According to another embodiment of the invention, the method further includes moving the one or more carriers along the track adjacent the upper belt with the plurality of upper magnets in a first direction and moving the one or more carriers along the track adjacent the lower belt with the plurality of lower magnets in a second direction orthogonal to the first direction.

This technology is particularly well-suited for, but by no means limited to, use with clinical analyzers for performing in vitro diagnostics (IVD).

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 1C is a top view of an exemplary modular sample tube transport system for use with embodiments of the present invention;

FIG. 2A is a cross sectional view at A-A of FIG. 1A illustrating a carrier positioned adjacent an upper magnet in accordance with an embodiment of the invention;

FIG. 2B is a cross sectional view at B-B of FIG. 1A illustrating a carrier positioned adjacent a lower magnet in accordance with an embodiment of the invention;

DETAILED DESCRIPTION OF ILLUSTRATIVE EMBODIMENTS

Embodiments of the present invention include systems and methods that provide a more efficient lab automation system for moving sample tube carriers between various modular testing stations with more positive control by utilizing alternating upper and lower conveyor systems having moving belts affixed with magnets. Embodiments of the present invention provide a sample tube transport system capable of being inexpensively scaled to add or remove modules for transporting carriers between various modular testing stations. Embodiments of the present invention provide a sample tube transport system that can transport the carriers along a path in both linear and non-linear directions.

Figure 1A:
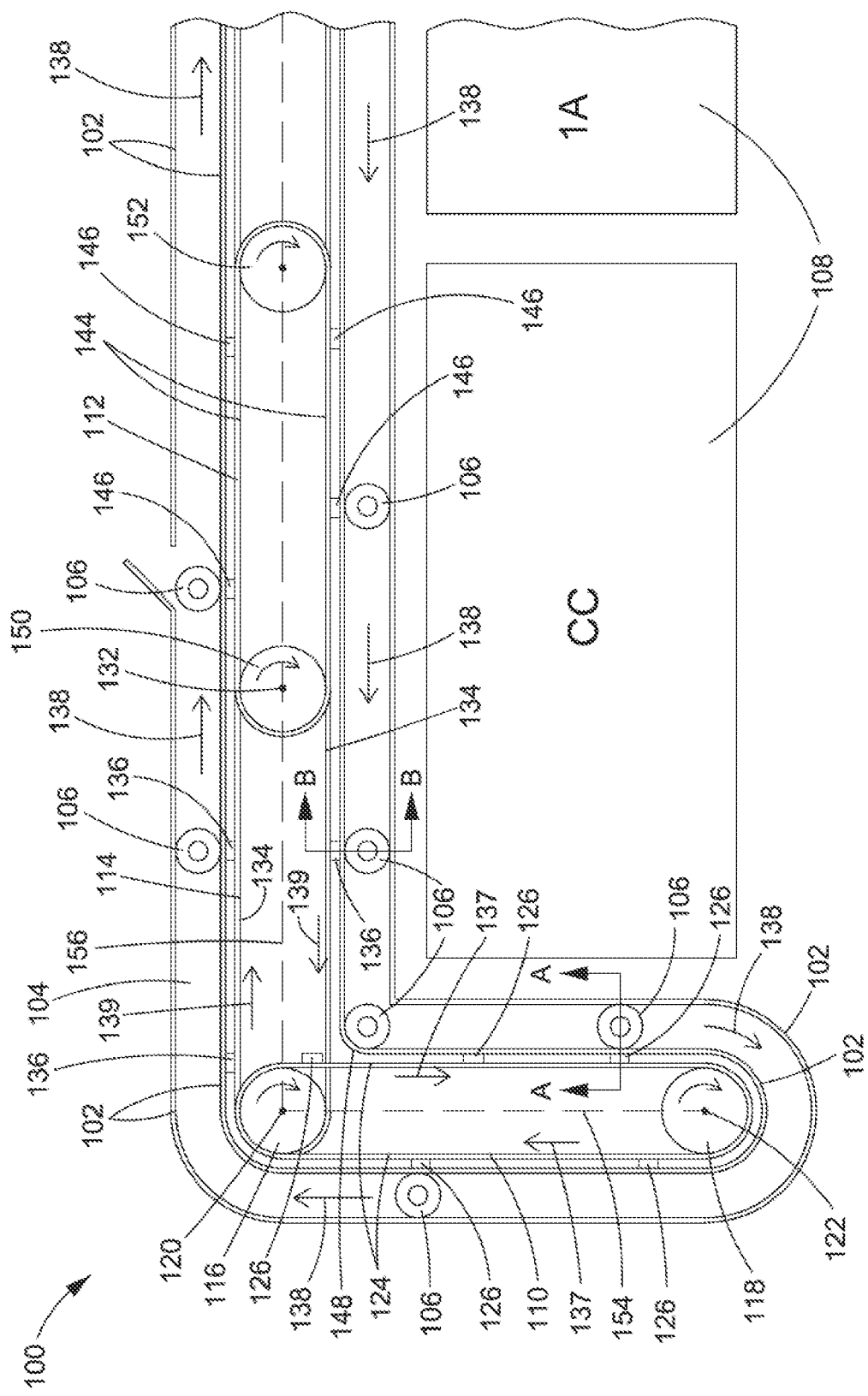
FIG. 1A is a top view of an exemplary modular sample tube transport system for use with embodiments of the present invention.
Figure 1B:
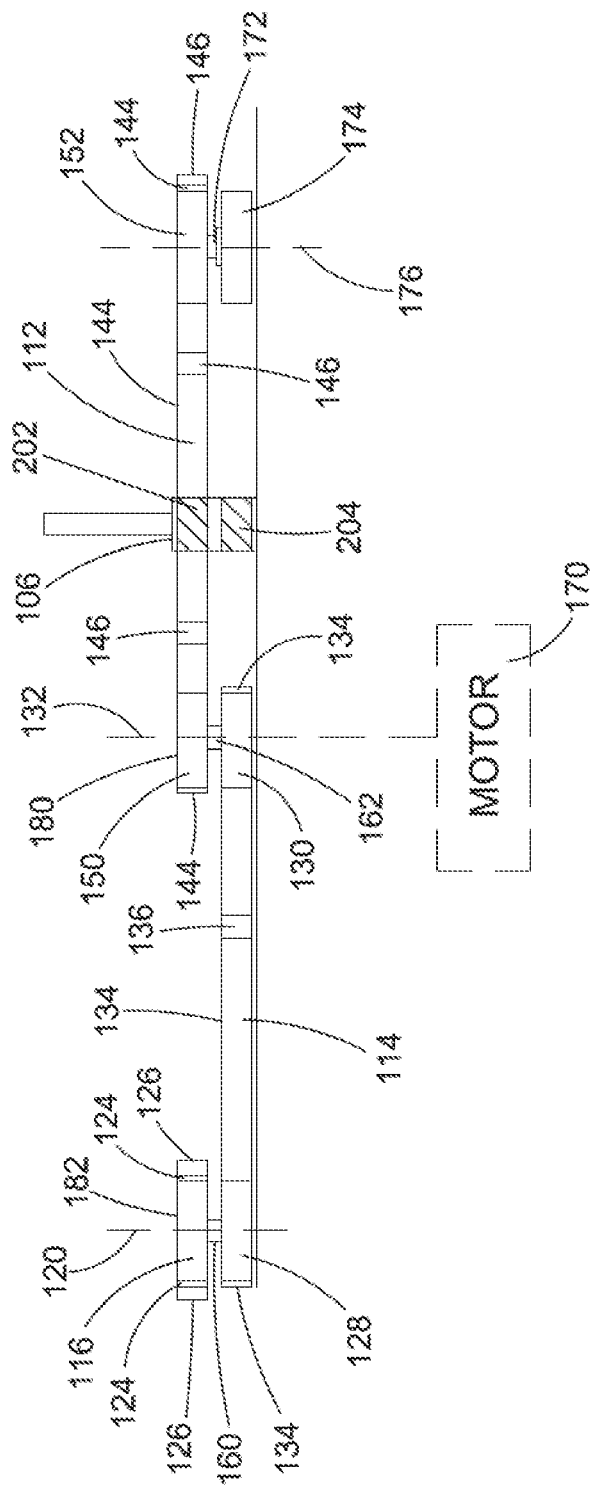
FIG. 1B is a partial side view of the exemplary modular sample tube transport system shown in FIG. 1A for use with embodiments of the present invention.

FIG. 1A is a top view of an exemplary modular sample tube transport system for use with embodiments of the present invention. FIG. 1B is a partial side view of the exemplary modular sample tube transport system shown in FIG. 1A for use with embodiments of the present invention. Referring to FIG. 1A, modular sample tube transport system 100 may include a track 102 adapted to provide a path 104 for carriers 106 between a plurality of modules 108. As used herein, the terms "module," "analyzer," and "instrument" include, but are not limited to, general chemistry, immunoassay, microbiology, molecular, hematology, and hemostasis analyzers, and automated pre- and post-analytical modules.

Modular sample tube transport system 100 may also include an upper conveyor system, such as first upper conveyor system 110 and a second upper conveyor system 112. First upper conveyor system 110 may include a first upper pulley 116 configured to rotate around a first axis 120 and a second upper pulley 118 spaced horizontally from the first upper pulley 116 and configured to rotate around a second axis 122. First upper conveyor system 110 may also include an upper belt 124 located adjacent the track 102 and configured to wrap around the first upper pulley 116 and around the second upper pulley 118. First upper conveyor system 110 may further include a plurality of upper magnets 126 affixed to the upper belt 124.

As shown in FIG. 1A, first upper pulley 116 and second upper pulley 118 may rotate clockwise around their respective axis 120, 122, causing upper magnets 126 to move with upper belt 124 around first upper pulley 116 and second upper pulley 118 in the direction shown by arrows 137. In some embodiments, first upper pulley 116 and second upper pulley 118 may rotate counter-clockwise around their respective axis 120, 122, causing upper magnets 126 to move with upper belt 124 around first upper pulley 116 and second upper pulley 118 in a direction opposite the direction shown by arrows 137.

Referring to FIG. 1A and FIG. 1B, modular sample tube transport system 100 may also include a lower conveyor system 114. As shown in FIG. 1A, lower conveyor system 114 may be orthogonal with first upper conveyor system 110. As shown in FIG. 1B, lower conveyor system 114 may include a first lower pulley 128 spaced vertically below the first upper pulley 116 and also configured to rotate around the first axis 120. Lower conveyor system 114 may also include a second lower pulley 130 spaced horizontally from the first lower pulley 128 and configured to rotate around a third axis 132. Lower conveyor system 114 may also include a lower belt 134 spaced vertically below the upper belt 124, located adjacent the track 102 and configured to wrap around the first lower pulley 128 and around the second lower pulley 130. Lower conveyor system 114 may further include a plurality of lower magnets 136 affixed to the lower belt 134.

In the embodiment shown in FIG. 1A and FIG. 1B, first lower pulley 128 and second lower pulley 130 also rotate clockwise around their respective axes 120, 132, causing lower magnets 136 to move with lower belt 134 around first lower pulley 128 and second lower pulley 130 in the direction shown by arrows 139. In some embodiments, first lower pulley 128 and second lower pulley 130 may rotate counter-clockwise around their respective axis 120, 132, causing lower magnets 136 to move with lower belt 134 around first lower pulley 128 and second lower pulley 130 in a direction opposite the direction shown by arrows 139.

FIG. 2A and FIG. 2B are cross sectional views of FIG. 1A illustrating the carrier 106 magnetically attracted to an upper magnet 126 and a lower magnet 136, respectively, in accordance with embodiments of the present invention. According to some embodiments, the plurality of upper magnets 126 may be positioned to attract carriers 106 for moving the carriers 106 along the track 102 adjacent the upper belt 124. For example, FIG. 2A is a cross sectional view at A-A of FIG. 1A illustrating one of the plurality of carriers 106 positioned adjacent one of the plurality of upper magnets 126 affixed to upper belt 124. As shown in FIG. 2A, a carrier 106 may include an upper portion of magnetic material 202 and a lower portion of magnetic material 204. In an aspect of an embodiment shown in FIG. 2A, upper portion of magnetic material 202 may be vertically offset from lower portion of magnetic material 204. Upper magnet 126 may be positioned such that when carrier 106 is proximate to the upper magnet 126, the upper portion of magnetic material 202 of carrier 106 and upper magnet 126 are magnetically attracted to each other, indicated by arrows 203. Accordingly, as upper magnet 126 moves with upper belt 124 around first upper pulley 116 and second upper pulley 118, carrier 106 is moved along track 102 adjacent the upper belt 124 in the direction indicated by directional arrows 138.

According to some embodiments, the plurality of lower magnets 136 may be positioned to attract the carriers 106 for moving the carriers 106 along the track 102 adjacent lower belt 134. For example, FIG. 2B is a cross sectional view at B-B of FIG. 1A illustrating one of the plurality of carriers 106 that is positioned adjacent one of the plurality of lower magnets 136 affixed to lower belt 134. As shown in FIG. 2B, a carrier 106 may include an upper portion of magnetic material 202 and a lower portion of magnetic material 204. Lower magnet 136 may be positioned such that when lower magnet 136 is proximate to the carrier 106, lower magnet 136 and the lower portion of magnetic material 204 of carrier 106 are magnetically attracted to each other, indicated by arrows 205.

According to some embodiments, as shown in FIG. 2A and FIG. 2B, the track 102 may include a bottom portion 206 extending horizontally between two opposing side walls 208. The side walls 208 may extend vertically from the bottom portion 206. The side walls 208 may include inner surface 210 and an outer surface 212. As shown in FIG. 2A, upper magnet 126 and upper portion of magnetic material 202 may become magnetically attracted to each other, as indicated by arrows 203, when upper magnet 126 is proximate to outer surface 212 and horizontally aligned with upper portion of magnetic material 202. Accordingly, carrier 106 may move toward inner surface 210 of the side wall 208 proximate upper magnet 126.

Likewise, as shown in FIG. 2B, lower magnet 136 and lower portion of magnetic material 204 may become magnetically attracted to each other, as indicated by arrows 205, when lower magnet 136 is proximate to outer surface 212 and horizontally aligned with lower portion of magnetic material 204. Accordingly, carrier 106 may move toward inner surface 210 of the side wall 208 proximate lower magnet 136.

In the embodiment shown in FIG. 2A and FIG. 2B, the distance between the opposing side walls may be greater than the width of the carrier 106. It is contemplated, however, that the width between the opposing side walls may be substantially equal to the width of the carrier 106.

In some embodiments, the track 102 may be formed of non-magnetic material (e.g., aluminum) or formed substantially from non-magnetic material. Further, the upper portion of magnetic material 202 and lower portion of magnetic material 204 may be formed of a magnetic material (i.e., ferrous material) or formed substantially from a magnetic material such that the magnetic attraction between carriers 106 and corresponding upper and lower magnets 126, 136 remains strong enough to transport the carriers 106 along the track 102.

In the embodiment shown in FIG. 1A, track 102 forms a continuous loop around a continuous belt system of alternating upper and lower belt systems 110, 112, 114. For example, first upper conveyor system 110 is configured to move a carrier 106 along track 102 adjacent the upper belt 124 in the direction indicated by directional arrows 138. The magnetic attraction between an upper magnet 126 and the upper portion of magnetic material 202 decreases as upper magnet 126 rotates around first upper pulley 116 and moves away from carrier 106. The magnetic attraction between a lower magnet 136 and the lower portion of magnetic material 204 increases as lower magnet 136 rotates around first lower pulley 128 and moves closer to carrier 106. Accordingly, the magnetic attraction becomes strong enough such that carrier 106 makes a 90 degree turn along track 102 and moves adjacent the lower belt 134 in the direction indicated by arrows 138.

As shown in FIG. 1A, the task of moving the carrier 106 along track 102 is switched from lower conveyor system 114 to second upper conveyor system 112. For example, the magnetic attraction between lower magnet 136 and the lower portion of magnetic material 204 begins to decrease as the lower magnet 136 rotates around second lower pulley 130 and moves away from carrier 106. The magnetic attraction between an upper magnet 146 of second upper conveyor system 112 and the upper portion of magnetic material 202 increases as upper magnet 146 rotates around first upper pulley 150 of second upper conveyor system 112 and moves closer to carrier 106. Accordingly, the magnetic attraction between upper magnet 146 and upper portion of magnetic material 202 becomes strong enough such that carrier 106 is moved along the track adjacent the second upper belt 144 of second upper conveyor system 112.

As shown in FIG. 1A, the transport system 100 is further configured such that carrier 106 may continue along track 102 past second upper pulley 152 and adjacent other alternating lower and upper conveyor systems (not shown). Carrier 106 eventually makes a 180 degree turn (e.g., loop around) until carrier 106 once again moves adjacent second upper belt 144. Carrier 106 continues on track 102 adjacent second upper belt 144 until the magnetic attraction between upper magnet 146 and the upper portion of magnetic material 202 decreases and the magnetic attraction between lower magnet 136 and the lower portion of magnetic material 204 becomes strong enough to move carrier 106 along the track 102 adjacent the lower belt 134. The magnetic attraction between lower magnet 136 and the lower portion of magnetic material 204 decreases as lower magnet 136 moves away from carrier 106 at corner 148. As shown in FIG. 1A, transport system 100 is configured to cause carrier 106 to turn 90 degrees as the magnetic attraction between an upper magnet 126 and the upper portion of magnetic material 202 again moves carrier 106 along the track adjacent the upper belt 124, completing the loop around track 102.

Embodiments of the present invention provide a sample tube transport system, such as sample tube transport system 100, which may be scaled to add or remove modules 108. The size, shape, and scale of the modular sample tube transport system 100 shown in the embodiment of FIG. 1A is exemplary. Further, the number of modules and types of modules of the modular sample tube transport system 100 shown in the embodiment of FIG. 1A is also exemplary.

Embodiments of the present invention may also include a modular sample tube transport system having a track 102 adapted to provide a path for carriers 106 between any number of modules 108. For example, as shown in the embodiment of FIG. 1C, modular sample tube transport system 100C may include a plurality of alternating upper and lower conveyor systems 190 adjacent track 102 that is adapted to provide a path for carriers 106 between modules 108. As shown in FIG. 1C, modules 108 may include sample handling (SH), clinical chemistry (CC), and immunoassay (IA) stations.

Figure 3:
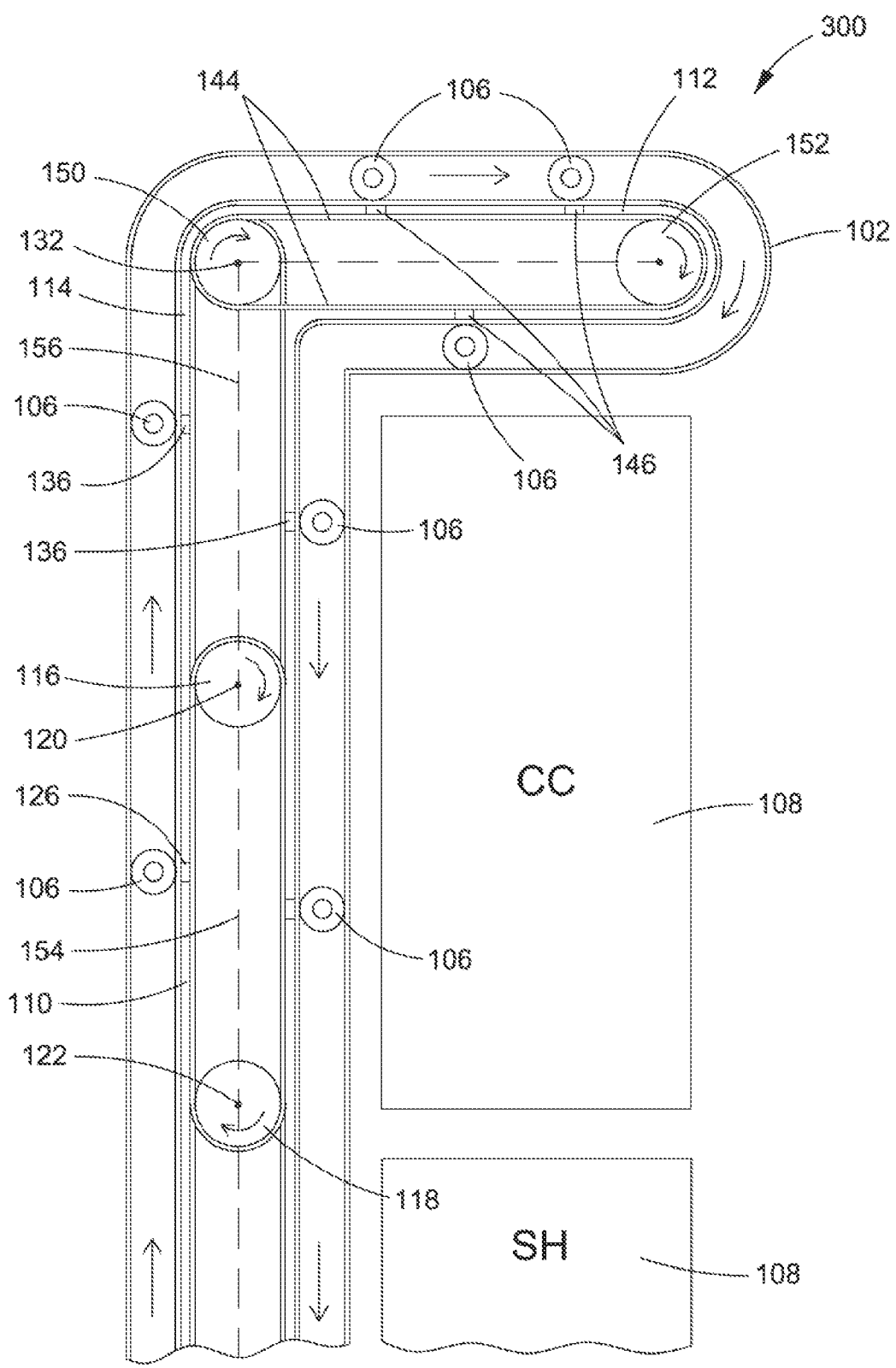
FIG. 3 is a top view of an exemplary modular sample tube transport system for use with embodiments of the present invention.

As shown in FIG. 1A, lower conveyor system 114 is orthogonal to first upper conveyor system 110 and collinear with second upper conveyor system 112. The sample transport system 100 in FIG. 1A may, however, be scaled to transport carriers 106 having a different modular configuration. For example, as shown in FIG. 3, lower conveyor system 114 has changed to be collinear with first upper conveyor system 110 and orthogonal to second upper conveyor system 112.

In some embodiments, upper and lower conveyor systems 110, 112, 114 may be oriented with each other in terms of their respective pulley axes 120, 122, 132. For example, in some embodiments, as shown in FIG. 1A, upper conveyor system 110 and lower conveyor system 114 are oriented to be orthogonal to each other in terms of their respective pulley axes 120, 122, 132. Referring to upper conveyor system 110 shown in FIG. 1A, first upper pulley 116 rotates around first axis 120 and second upper pulley 118 rotates around second axis 122. Further, first axis 120 and the second axis 122 are arranged such that an upper conveyor system line 154 extends between the first axis 120 and the second axis 122. Referring to the lower conveyor system 114 shown in FIG. 1B, first lower pulley 128 rotates around the first axis 120 (common to first upper pulley 116 and first lower pulley 128) and second lower pulley 130 rotates around third axis 132. Further, the first axis 120 and the third axis 132 are arranged such that a lower conveyor system line 156 extends between the first axis 120 and the third axis 132. As shown in FIG. 1A, upper conveyor system line 154 and the lower conveyor system line 156 are orthogonal to each other. Accordingly, transport system 100 may be configured to cause carrier 106 to turn 90 degrees, as described above. In some embodiments, however, the upper conveyor system line 154 may extend from the lower conveyor system line 156 at any angle greater than 0 degrees and less than 180 degrees, including an angle of 90 degrees, as shown in FIG. 1A. Accordingly, an exemplary transport system may be configured to cause carrier 106 to turn along the track 102 at different angles, such as the 90 degree turn shown in FIG. 1A.

In some embodiments, an upper conveyor system 110 and a lower conveyor system 114 may be oriented to be collinear with each other in terms of their respective pulley axes 120, 122, 132. For example, as shown in FIG. 3, transport system 300 also includes upper conveyor system line 154 extending between the first axis 120 and the second axis 122 and lower conveyor system line 156 extending between the first axis 120 and the third axis 132. As shown in FIG. 3, the upper conveyor system line 154 and the lower conveyor system line 156 are collinear with each other. Accordingly, an exemplary transport system may be configured to cause carrier 106 to remain straight along the track from one conveyor system to another.

Embodiments of the present invention may also be described in terms of a plurality of pulley assemblies 180, 182 coupled between alternating upper and lower conveyor systems 110, 112, 114 moving around corresponding pulley assemblies 180, 182. For example, as shown in FIGS. 1A and 1B, conveyor systems alternate between first upper conveyor system 110, lower conveyor system 114, and second upper conveyor system 112. Pulley assembly 180 is coupled between lower conveyor system 114 and second upper conveyor system 112 and includes lower pulley 130 and a upper pulley 150. Pulley assembly 182 is coupled between lower conveyor system 114 and first upper conveyor system 110 and includes upper pulley 116 and lower pulley 128.

In some embodiments, a pulley assembly, such as assemblies 180, 182, may also include a shaft, such as shafts 160 and 162. As shown in FIG. 1B, shaft 162 is coupled to upper pulley 150 (of second upper conveyor system 112) and the lower pulley 130 (of lower conveyor system 114) and configured to rotate around axis 132. Shaft 160 is coupled to upper pulley 116 (of first upper conveyor system 110) and lower pulley 128 (of lower conveyor system 114) and configured to rotate around axis 120.

Figures 4A, 4B:
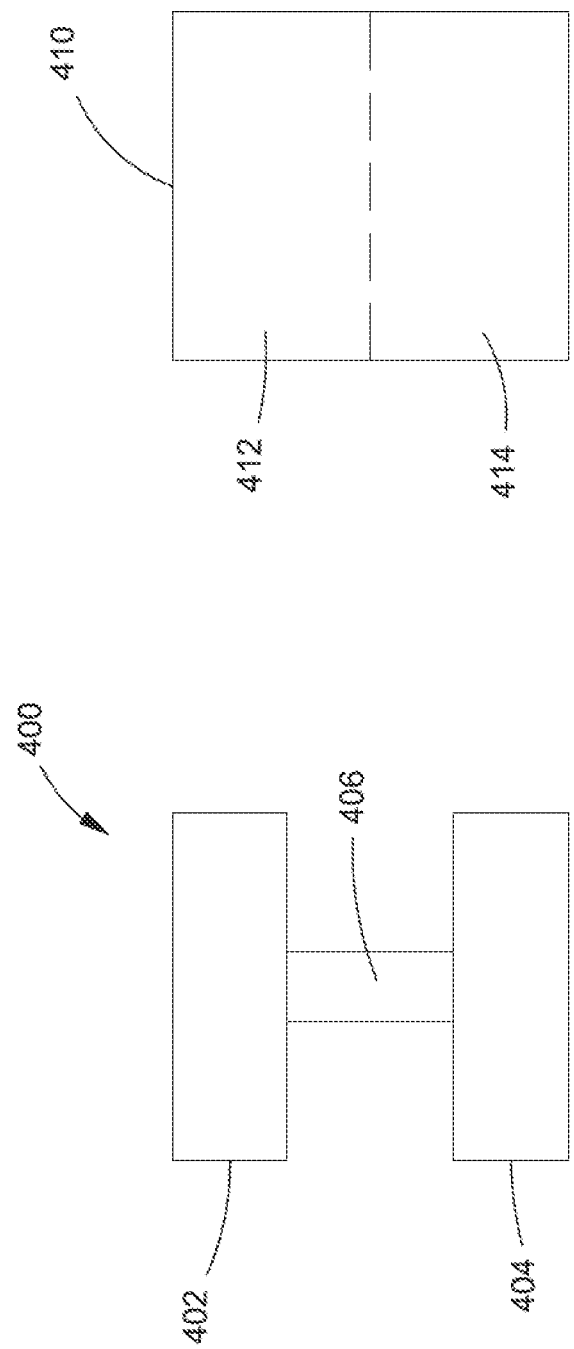
FIG. 4A is a side view of an exemplary pulley assembly having a shaft coupled between an upper pulley and a lower pulley in accordance with an embodiment of the invention.
FIG. 4B is a side view of an exemplary pulley assembly illustrating a contiguous pulley portion having an upper pulley and a lower pulley in accordance with an embodiment of the invention.

In one aspect of an embodiment, as shown in FIG. 4A, a pulley assembly 400 may include an upper pulley 402 vertically offset from lower pulley 404. Shaft 406 may be coupled between upper pulley 402 and lower pulley 404. An upper belt, such as upper belt 124 and 144, may be configured to wrap around upper pulley 402 and a lower belt, such as lower belt 134, may be configured to wrap around lower pulley 404. In another aspect of an embodiment, as shown in FIG. 4B, pulley assembly 410 may include a contiguous pulley portion having an upper pulley 412 and a lower pulley 414. An upper belt, such as upper belt 124 and 144, may be configured to wrap around upper pulley 412 and a lower belt, such as lower belt 134, may be configured to wrap around lower pulley 414.

In an aspect of an embodiment, a plurality of coupled conveyor systems, such as conveyor systems 110, 112, and 114 may be driven by a single actuation device such as motor 170. For example, as shown in FIG. 1B, shaft 162 may be a drive shaft that is coupled to motor 170 for driving conveyor systems 110, 112, and 114. That is, drive shaft 162 may be coupled to motor 170 and configured to rotate upper pulley 150 (of upper conveyor system 112) around axis 132 and also rotate lower pulley 130 (of lower conveyor system 114) around axis 132. Responsive to the rotation of the drive shaft 162 by the motor 170, upper pulley 150 may rotate around the axis 132, causing the upper belt 144 to wrap around upper pulley 150 and around the opposing upper pulley 152 (of upper conveyor system 112). Responsive to the rotation of the drive shaft 162 by the motor 170, the lower pulley 130 may also rotate around the axis 132, causing the lower belt 134 to wrap around lower pulley 130 and around opposing lower pulley 128. Responsive to the rotation of opposing lower pulley 128, shaft 160 may rotate around axis 120, causing upper pulley 116 (of upper conveyor system 110) also to rotate around axis 120. The rotation of upper pulley 116 may also cause upper belt 124 to wrap around upper pulley 116 and around the opposing upper pulley 118 (of upper conveyor system 110).

In another aspect of an embodiment, an auxiliary motor (not shown) may be added to drive any number of coupled conveyor systems. For example, an auxiliary motor may be added when a number of coupled conveyor systems exceeds a predetermined number of coupled conveyor systems or when a force, required to drive a number of coupled conveyor systems, exceeds a predetermined force threshold.

In another aspect of an embodiment, for a pulley 152 having no adjacent conveyor system, a coupling device 172 may be used to couple pulley 152 to a device 174. Device 174 may be a stationary device that is not configured to rotate around axis 176. Device 174 and coupling device 172 may be replaced with a rotatable shaft and a rotatable pulley if another conveyor system is added. It is also contemplated that a pulley having no adjacent conveyor system, such as pulley 152, may be coupled to a rotatable shaft and another vertically displaced pulley (capable of being used in a newly added conveyor system) so that device 174 and coupling device 172 need not be replaced with a rotatable shaft and rotatable pulley if another conveyor system is added.

Figure 5:
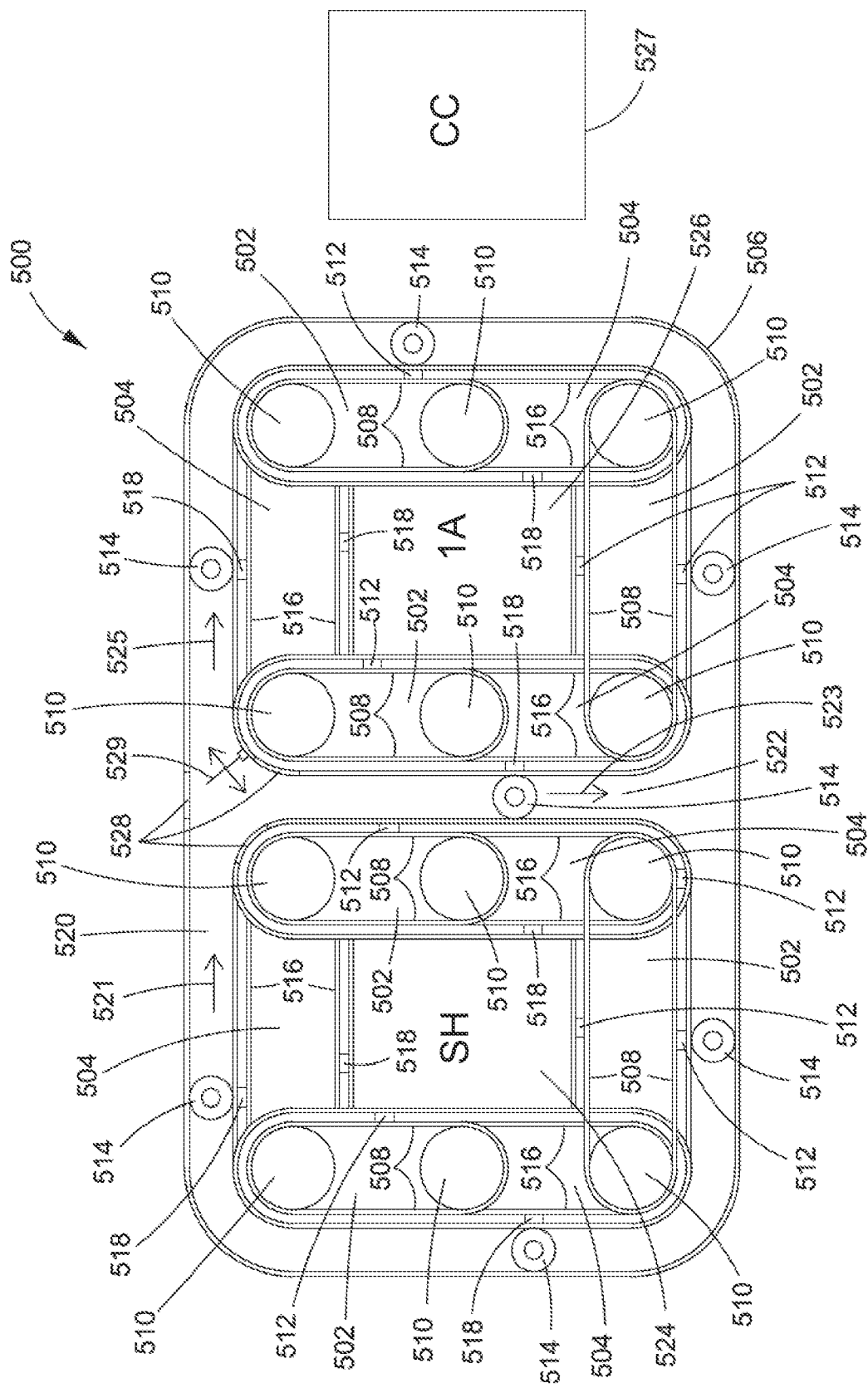
FIG. 5 is a top view of an exemplary modular sample tube transport system for use with embodiments of the present invention.

Exemplary transport systems may include alternating upper and lower conveyor systems oriented in a variety of ways. For example, as shown in FIG. 5, modular sample tube transport system 500 may include a plurality of conveyor systems alternating between respective upper conveyor systems 502 and adjacent respective lower conveyor systems 504. Upper conveyor systems 502 each include upper belt 508 located adjacent the track 506 and configured to wrap around corresponding upper pulleys 510. Each upper conveyor system 502 also includes a plurality of upper magnets 512 affixed to the upper belt 508 and positioned to attract the one or more carriers 514 for moving the one or more carriers 514 along the track 506. Each lower conveyor system 504 includes a lower belt 516 located adjacent the track 506 and configured to wrap around corresponding upper pulleys (not shown). Each lower conveyor system 504 also includes a plurality of lower magnets 518 affixed to the lower belt 516 and positioned to attract the one or more carriers 514 for moving the one or more carriers 514 along the track 506.

Exemplary transport systems having alternating upper and lower conveyor systems may include a variety of geometric configurations. For example, according to some embodiments as shown in FIG. 5, a track 506 may include paths 520, 522 between and around modules 524, 526, 527. Track 506 includes a first path 520 and second path 522 orthogonal to the first path 520. According to the embodiment shown in FIG. 5, transport system 500 may be configured such that a lower conveyor system having lower magnets 518 may move the one or more sample carriers 514 along the first path 520 in the direction indicated by arrow 521. Further, transport system 500 may be configured such that both a lower conveyor system having lower magnets 518 and an upper conveyor system having upper magnets 512 may move the one or more sample carriers 514 along the second path 522 between modules 524 and 526 in the direction indicated by arrow 523.

The size, shape, and scale of the modular sample tube transport system 500 shown in the embodiment of FIG. 5 is exemplary. For example, in some exemplary embodiments, the modules may be larger than the modules shown in FIG. 5, and two or more alternating upper and lower conveyor systems may be positioned adjacent to each side of the modules. Further, exemplary embodiments may include any number of modules and types of modules.

According to some embodiments, a modular sample tube transport system 500 may include a switching gate 528, 529 located proximate to the intersection of the first path 520 and the second path 522 and configured to cause the one or more sample carriers 514 to move along the first path 520 or move along the second path 522. For example, in one aspect of the embodiment, the switching gate may include a mechanical gate 529 that may be actuated electrically, hydraulically, pneumatically, etc. The actuation of the mechanical gate 529 may be responsive to a wired or wireless signal. The signal may be electrical, optical, electro-magnetic, etc. The mechanical gate 529 may be configured to move in directions such that the one or more sample carriers 514 moves along the first path 520 in the direction indicated by arrow 525 or moves along the second path 522 in the direction indicated by arrow 523.

In another aspect of the embodiment, the switching gate may include a magnetic gate 528 that may be located at different positions proximate to the intersection of the first path 520 and the second path 522 as shown in FIG. 5. At any of the positions shown in FIG. 5, the magnetic gate 528 may produce a magnetic force stronger than the magnetic force of the upper and lower magnets 512, 518 such that the one or more sample carriers 514 moves along the first path 520 in the direction indicated by arrow 525 or moves along the second path 522 in the direction indicated by arrow 523. The movement of the mechanical gate 529 and the amount of magnetic force produced by the magnetic gate 528 may be controlled by a controller (not shown). The controller may move the mechanical gate 529 and/or cause the magnetic gate 528 to produce an amount of magnetic force based on received operating conditions.

Figure 6:
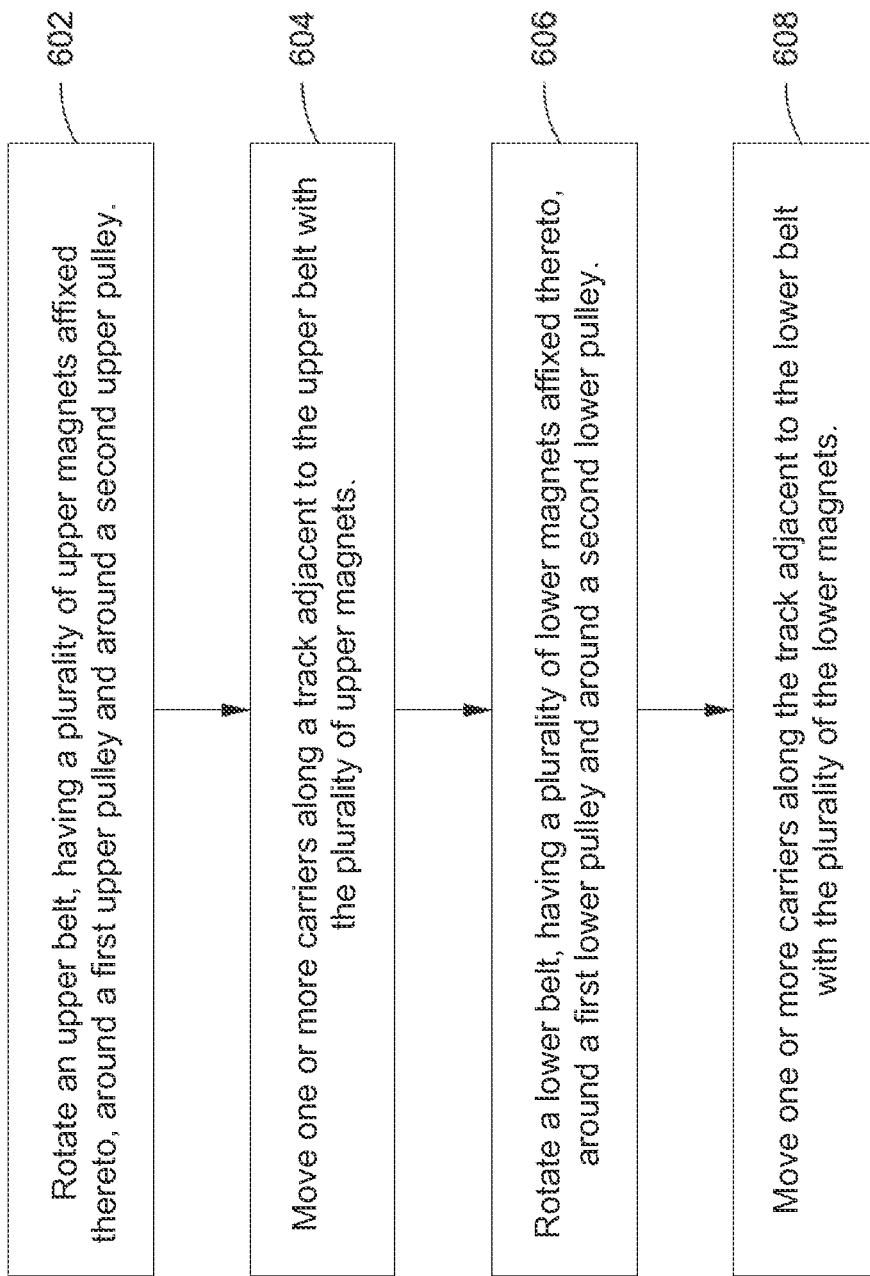
FIG. 6 is a flow chart illustrating a method for transporting sample tubes in accordance with an embodiment of the invention.

FIG. 6 is a flow chart illustrating an exemplary method for controlling operation of a sample tube transport system in accordance with an embodiment of the invention. As shown at block 602, the method may include rotating an upper belt 124 having a plurality of upper magnets 126 affixed thereto, around a first upper pulley 116 and around a second upper pulley 118 by rotating the first upper pulley 116 around a first axis 120 and rotating the second upper pulley 118 around a second axis 122. At block 604, the method may include moving one or more carriers 106 along a track 102 adjacent the upper belt 124 with the plurality of upper magnets 126. For example, first upper conveyor system 110 is configured to move a carrier 106 along track 102 adjacent the upper belt 124 in the direction indicated by directional arrows 138. The magnetic attraction between an upper magnet 126 and the upper portion of magnetic material 202 decreases as upper magnet 126 rotates around first upper pulley 116 and moves away from carrier 106.

As shown at block 606, the method may include rotating a lower belt 134, having a plurality of lower magnets 136 coupled thereto, around a first lower pulley 128 and around a second lower pulley 130 by rotating the first lower pulley 128 around the first axis 120 and rotating the second lower pulley 130 around a third axis 132. At block 608, the method may include moving the one or more carriers 106 along the track 102 adjacent the lower belt 134 with the plurality of lower magnets 136. The magnetic attraction between a lower magnet 136 and the lower portion of magnetic material 204 increases as lower magnet 136 rotates around first lower pulley 128 and moves closer to carrier 106. Accordingly, the magnetic attraction becomes strong enough such that carrier 106 makes a 90 degree turn along track 102 and moves adjacent the lower belt 134 in the direction indicated by arrows 138.

As described above, the carrier 106 continues to move along track 102 by alternating upper and lower conveyor systems 110, 112, 114, making a 180 degree turn around pulley 152, and making another 90 degree turn at corner 148 until the carrier 106 completes the loop around track 102.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed:

1. A sample tube transport system comprising:
a track adapted to provide a path for one or more carriers between a plurality of modules;
at least one upper conveyor system comprising:
a first upper pulley configured to rotate around a first axis;
a second upper pulley spaced horizontally from the first upper pulley and configured to rotate around a second axis;
an upper belt located adjacent the track and configured to wrap around the first upper pulley and around the second upper pulley; and
a plurality of upper magnets affixed to the upper belt, each of the plurality of upper magnets being positioned to attract the one or more carriers for moving the one or more carriers along the track adjacent the upper belt; and
at least one lower conveyor system comprising:
a first lower pulley spaced vertically below the first upper pulley and configured to rotate around the first axis;
a second lower pulley spaced horizontally from the first lower pulley and configured to rotate around a third axis;
a lower belt spaced vertically below the upper belt, located adjacent the track and configured to wrap around the first lower pulley and around the second lower pulley; and
a plurality of lower magnets affixed to the lower belt, each of the plurality of lower magnets being positioned to attract the one or more carriers for moving the one or more carriers along the track adjacent the lower belt.

2. The sample tube transport system of claim 1, wherein
the plurality of upper magnets are further positioned such that an upper portion of magnetic material of the one or more carriers is attracted to a corresponding upper magnet for moving the one or more carriers along the track adjacent the upper belt; and
the plurality of lower magnets are further positioned such that a lower portion of magnetic material of the one or more carriers is attracted to a corresponding lower magnet for moving the one or more carriers along the track adjacent the lower belt.

3. The sample tube transport system of claim 2, wherein the upper portion of magnetic material is vertically offset from the lower portion of magnetic material.

4. The sample tube transport system of claim 1, wherein
the first axis and the second axis are arranged to form an upper conveyor system line extending between the first axis and the second axis;
the first axis and the third axis are arranged to form a lower conveyor system line extending between the first axis and the third axis; and
the upper conveyor system line extends from the lower conveyor system line at any angle greater than 0 degrees and less than 180 degrees.

5. The sample tube transport system of claim 1, wherein
the first axis and the second axis are arranged to form an upper conveyor system line extending between the first axis and the second axis;
the first axis and the third axis are arranged to form a lower conveyor system line extending between the first axis and the third axis; and
the upper conveyor system line extends from the lower conveyor system line at any angle of about 90 degrees.

6. The sample tube transport system of claim 1, wherein
the first axis and the second axis are arranged to form an upper conveyor system line extending between the first axis and the second axis;
the first axis and the third axis are arranged to form a lower conveyor system line extending between the first axis and the third axis; and
the upper conveyor system line and the lower conveyor system line are collinear.

7. The sample tube transport system of claim 1, further comprising a shaft coupled to the first upper pulley and the first lower pulley and configured to rotate around the first axis.

8. The sample tube transport system of claim 7, wherein the shaft is a drive shaft coupled to an actuation device and configured to rotate the first upper pulley around the first axis and rotate the first lower pulley around the first axis.

9. A modular sample tube transport system comprising:
a plurality of modules for conducting processing on one or more samples;
a track configured to provide at least one path for one or more sample carriers between the plurality of modules;
a plurality of conveyor systems comprising at least one upper conveyor system and at least one lower conveyor system, and
one or more pulley assemblies configured to be coupled between the at least one upper conveyor system and the at least one lower conveyor system, the one or more pulley assemblies having an upper pulley and a lower pulley,
wherein
the plurality of conveyor systems alternate between a respective upper conveyor system and an adjacent respective lower conveyor system,
the at least one upper conveyor system comprises:
an upper belt located adjacent the track and configured to wrap around corresponding upper pulleys of the plurality of pulley assemblies; and
a plurality of upper magnets affixed to the upper belt and positioned to attract the one or more carriers for moving the one or more carriers along the track, and
at least one adjacent lower conveyor system comprises:
a lower belt located adjacent the track and configured to wrap around corresponding lower pulleys of the plurality of pulley assemblies; and
a plurality of lower magnets affixed to the lower belt and positioned to attract the one or more carriers for moving the one or more carriers along the track.

10. The modular sample tube transport system of claim 9, wherein
the plurality of upper magnets are further positioned such that an upper portion of magnetic material of the one or more carriers is attracted to a corresponding upper magnet for moving the one or more carriers along the track adjacent the upper belt, and
the plurality of lower magnets are further positioned such that a lower portion of magnetic material of the one or more carriers is attracted to a corresponding lower magnet for moving the one or more carriers along the track adjacent the lower belt.

11. The modular sample tube transport system of claim 9, wherein the respective upper conveyor system is non-linear to the adjacent respective lower conveyor system.

12. The modular sample tube transport system of claim 11, wherein the respective upper conveyor system is orthogonal to the adjacent respective lower conveyor system.

13. The modular sample tube transport system of claim 9, wherein the respective upper conveyor system is collinear to the adjacent respective lower conveyor system.

14. The modular sample tube transport system of claim 9, wherein the one or more pulley assemblies includes a common shaft coupled between the upper pulley and the lower pulley.

15. The modular sample tube transport system of claim 14, wherein the common shaft is a drive shaft coupled to an actuation device and configured to rotate the upper pulley and the lower pulley.

16. The modular sample tube transport system of claim 9, wherein the track comprises:
a bottom portion; and
opposing side walls spaced from each other and extending vertically from the bottom portion,
wherein at least one of the upper magnets and lower magnets moves parallel with a portion of at least one opposing side wall for moving the one or more carriers along the track.

17. The modular sample tube transport system of claim 16, further comprising at least one path switching gate,
wherein
the plurality of modules comprises a first module and a second module,
the at least one path comprises a first path and a second path,
the second path extends between the first module and the second module, and
the at least one switching gate is located proximate to the intersection of the first path and the second path and is configured to cause the one or more sample carriers to move along the first path or move along the second path.

18. A method for transporting sample tubes comprising:
rotating an upper belt, having a plurality of upper magnets affixed thereto, around a first upper pulley and around a second upper pulley by rotating the first upper pulley around a first axis and rotating the second upper pulley around a second axis;
moving one or more carriers along a track adjacent the upper belt with the plurality of upper magnets;

rotating a lower belt, having a plurality of lower magnets affixed thereto, around a first lower pulley and around a second lower pulley by rotating the first lower pulley around the first axis and rotating the second lower pulley around a third axis;

moving the one or more carriers along the track adjacent the lower belt with the plurality of lower magnets.

19. The method of claim 18, wherein moving the one or more carriers along the track adjacent the upper belt with the plurality of upper magnets further comprises attracting upper portions of magnetic material of corresponding carriers to respective upper magnets, and moving the one or more carriers along the track adjacent the lower belt with the plurality of lower magnets further comprises attracting lower portions of magnetic material of corresponding carriers to respective lower magnets.

20. The method of claim 19, further comprising:

moving the one or more carriers along the track adjacent the upper belt with the plurality of upper magnets in a first direction; and moving the one or more carriers along the track adjacent the lower belt with the plurality of lower magnets in a second direction orthogonal to the first direction.

* * * * *